(12) United States Patent
Kamen et al.

(10) Patent No.: US 11,450,431 B2
(45) Date of Patent: Sep. 20, 2022

(54) METHOD TO IDENTIFY OPTIMUM CORONARY ARTERY DISEASE TREATMENT

(71) Applicants: Ali Kamen, Skillman, NJ (US); Maneesh Kumar Singh, Lawrenceville, NJ (US); Sebastian Poelsterl, Munich (DE); Lance Anthony Ladic, Robbinsville, NJ (US); Dorin Comaniciu, Princeton Junction, NJ (US)

(72) Inventors: Ali Kamen, Skillman, NJ (US); Maneesh Kumar Singh, Lawrenceville, NJ (US); Sebastian Poelsterl, Munich (DE); Lance Anthony Ladic, Robbinsville, NJ (US); Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 649 days.

(21) Appl. No.: 14/442,517

(22) PCT Filed: Nov. 15, 2013

(86) PCT No.: PCT/US2013/070225
§ 371 (c)(1),
(2) Date: May 13, 2015

(87) PCT Pub. No.: WO2014/078615
PCT Pub. Date: May 22, 2014

(65) Prior Publication Data
US 2016/0292372 A1 Oct. 6, 2016

Related U.S. Application Data

(60) Provisional application No. 61/727,255, filed on Nov. 16, 2012.

(51) Int. Cl.
*G06N 3/04* (2006.01)
*G06N 3/08* (2006.01)
(Continued)

(52) U.S. Cl.
CPC ............ *G16H 50/20* (2018.01); *G06N 3/0472* (2013.01); *G06N 3/08* (2013.01); *G16Z 99/00* (2019.02)

(58) Field of Classification Search
CPC ....... G06F 19/345; G06N 3/0472; G06N 3/08
(Continued)

(56) References Cited

U.S. PATENT DOCUMENTS 4,566,459 A 1/1986 Umemura et al.
4,781,199 A 11/1988 Hirama et al.
(Continued)

OTHER PUBLICATIONS

Valgimigli, et al., "Cyphering the Complexity of Coronary Artery Disease Using the Syntax Score to Predict Clinical Outcome in Patients With Three-Vessel Lumen Obstruction Undergoing Percutaneous Coronary Intervention", American Journal of Cardiology, vol. 99, Issue 8, Apr. 15, 2007, pp. 1072-1081.*
(Continued)

*Primary Examiner* — Daniel T Pellett (57) ABSTRACT

A method of identifying an optimum treatment for a patient suffering from coronary artery disease, comprising: (i) providing patient information selected from: (a) status in the patient of one or more coronary disease associated biomarkers; (b) one or more items of medical history information selected from prior condition history, intervention history and medication history; (c) one or more items of diagnostic history, if the patient has a diagnostic history; and (d) one or more items of demographic data; (ii) aggregating the patient information in: (a) a Bayesian network; (b) a machine learning and neural network; (c) a rule-based system; and (d) a regression-based system; (iii) deriving a predicted proba-
(Continued)

bilistic adverse event outcome for each intervention comprising percutaneous coronary intervention by placement of a bare metal stent, or a drug-coated stent; or by coronary artery bypass grafting; and (iv) determining the intervention having the lowest predicted probabilistic adverse outcome.

15 Claims, 2 Drawing Sheets

(51) Int. Cl.
    *G16H 50/20*     (2018.01)
    *G16Z 99/00*     (2019.01)
(58) Field of Classification Search
    USPC .......................................................... 705/25
    See application file for complete search history.

(56) References Cited

U.S. PATENT DOCUMENTS

| | | | | |
|---|---|---|---|---|
| 4,852,577 | A | 8/1989 | Smith et al. | |
| 6,556,977 | B1* | 4/2003 | Lapointe | G06F 19/345 706/15 |
| 6,719,695 | B2 | 4/2004 | Bae et al. | |
| 2005/0203773 | A1* | 9/2005 | Soto | G06F 19/3431 705/2 |
| 2007/0167687 | A1 | 7/2007 | Annest | |
| 2008/0091471 | A1* | 4/2008 | Michon | G16H 50/70 705/3 |
| 2008/0118924 | A1* | 5/2008 | Buechler | G01N 33/74 435/6.11 |
| 2009/0177495 | A1* | 7/2009 | Abousy | G06F 19/345 705/3 |
| 2010/0273738 | A1* | 10/2010 | Valcke | A61B 5/02152 514/56 |
| 2015/0134047 | A1* | 5/2015 | McClain | A61L 31/10 623/1.42 |

OTHER PUBLICATIONS

The Task Force on Myocardial Revascularization of the European Society et al., "Guidelines on myocardial revascularization", European Journal of Cardio-thoracic Surgery 38, S1 (2010) S1-S52.*
Gershlick, et al., "PCI or CABG: which patients and at what cost?", www.heartjnl.com, May 28, 2008.*
Rothschild, et al., "DES vs. BMS—Which Are Best?", DAIC, Jul. 9, 2008.*
Medical-Dictionary, https://medical-dictionary.thefreedictionary.com/cascade+testing.*
Ben-Dor et al., "The Cureent Role of Bare-Metal Sternts: An evaluation of the importance of BMS in contemporary practice", Cardiac Interventions Today, Jan. / Feb. 2011.*
Serruys, et al., "Impact of Stent Thrombosis on Mace in the ARTS-II Study", Circulation.2007; 116:II_566.*
Ceconi et al., "ACE inhibition with perindopril and biomarkers of atherosclerosis and thrombosis: Results from the PERTINENT study", Atherosclerosis 204 (2009) 273-275.*
Kucher, et al., "Cardiac Biomarkers for Risk Stratification of Patients with Acute Pulmonary Embolism", Circulation, Nov. 4, 2003.*
Hannan, et al., "Generalized Regression Neural Network and Radial Basis Function for Heart Disease Diagnosis", International Journal of Computer Application (0975-8887) vol. 7—No. 13, Oct. 2010 (Year: 2010).*
Chong et al; "Stratification of adverse outcomes by preoperative risk factors in coronary artery bypass graft patients: an artificial neural network prediction model"; AMIA Annual Symposium proceedings /AMIA Symposium; pp. 160-164; XP055115106; 2003; US.

Resnic et al; "Simplified risk score models accurately predict the risk of major in-hospital complications following percutaneous coronary intervention"; The American Journal of Cardiology; vol. 88; No. 1; pp. 5-9; ISSN: 0002-9149; DOI: 10.1016/S0002-9149(01)01576-4; XP055115316; 2001; Jul. 1, 2001.
Farooq et al; "The SYNTAX Score and SYNTAX-Based Clinical Risk Scores"; Seminars in thoracic and cardiovascular surgery; vol. 23; No. 2; pp. 99-105; ISSN: 1043-0679; DOI: 10.1053/J.SEMTCVS. 2011.08.001; XP028331170; 2011.
Ruß et al.; "Different treatment options in chronic coronary artery disease: when is it the time for medical treatment, , percutaneous coronary intervention or aortocoronary bypass surgery?"; Deutsches Ärzteblatt international; vol. 106; No. 15; pp. 253-261; DOI: 10.3238/arztebl.2009.0253; XP055115289; 2009; Apr. 10, 2009.
The Task Force on Myocardial Revascularization of the European Society et al; "Gudelines on myocardial revascularization"; European journal of cardio-Thoracic surgery, Springer Verlag Berlin; vol. 38; pp. s1-S52; ISSN: 1010-7940; XP027459607; 2010.
Fleisher et al; "ACC/AHA 2007 Guidelines on Perioperative Cardiovascular Evaluation and Care for Noncardiac Surgery"; Journal of the american college of Cardiology, Elsevier; vol. 50; No. 17; pp. e159-e242; ISSN: 0735-1097 DOI: 10.1016/JJACC.2007.09.003; XP024338884; 2007; Oct. 23, 2007.
Damman, Peter, et al. "Multiple biomarkers at admission significantly improve the prediction of mortality in patients undergoing primary percutaneous coronary intervention for acute ST-segment elevation myocardial infarction." Journal of the American College of Cardiology 57.1 (2011): 29-36.
Mehran, Roxana, et al. "Angiographic patterns of in-stent restenosis: classification and implications for long-term outcome." Circulation 100.18 (1999): 1872-1878.
Stankovic, Goran, et al. "Prediction of restenosis after coronary angioplasty by use of a new index: TIMI frame count/minimal luminal diameter ratio." Circulation 101.9 (2000): 962-968.
Denny Jr, Donald F. "Prediction of restenosis after carotid artery stent implantation." Radiology 227.2 (2003): 316-318.
Hannan, Edward L., et al. "Long-term outcomes of coronary-artery bypass grafting versus stent implantation." New England Journal of Medicine 352.21 (2005): 2174-2183.
Hermus, Linda, et al. "Carotid plaque formation and serum biomarkers." Atherosclerosis 213.1 (2010): 21-29.
Jensen, Matt B., et al. "The promise and potential pitfalls of serum biomarkers for ischemic stroke and transient schemic attack." The neurologist 14.4 (2008): 243.Jensen.
Dangas, George, and Frank Kuepper. "Restenosis: repeat narrowing of a coronary artery: prevention and treatment." Circulation 105.22 (2002): 2586-2587.
Hilty, K. Chad, and Daniel H. Steinberg. "Vulnerable plaque imaging—current techniques." Journal of cardiovascular translational research 2.1 (2009): 9-18.
Costa, Marco A., and Daniel I. Simon. "Molecular basis of restenosis and drug-eluting stents." Circulation 111.17 (2005): 2257-2273.
Schömig, Albert, Adnan Kastrati, and Rainer Wessely. "Prevention of restenosis by systemic drug therapy: back to the future?." (2005): 2759-2761.
Wessely, Rainer, Albert Schömig, and Adnan Kastrati. "Sirolimus and paclitaxel on polymer-based drug-eluting stents: similar but different." Journal of the American College of Cardiology 47.4 (2006): 708-714.
Van Tiel, Claudia M., et al. "p27kip1-838C> A single nucleotide polymorphism is associated with restenosis risk after coronary stenting and modulates p27kip1 promoter activity." Circulation 120.8 (2009): 669-676.
Chan, D. and Ng, L.L., 2010. Biomarkers in acute myocardial infarction. BMC medicine, 8:34.
Trikalinos, T. A., et al. "Future Research Needs for the Comparison of Percutaneous Coronary Interventions with Bypass Graft Surgery in Nonacute Coronary Artery Disease: Identification of Future Research Needs from Comparative Effectiveness Review No. 9." (2010); Agency for Healthcare Research and Quality (US).
Yeh, Robert W., et al. "Predicting the restenosis benefit of drug-eluting versus bare metal stents in percutaneous coronary intervention." Circulation (2011): CIRCULATIONAHA-111.

(56) References Cited

OTHER PUBLICATIONS

Yock, Cynthia A., et al. "Cost-effectiveness of bypass surgery versus stenting in patients with multivessel coronary artery disease." The American journal of medicine 115.5 (2003): 382-389.
Bischof, Matthias, Matthias Briel, Heiner C. Bucher, and Alain Nordmann. "Cost-effectiveness of drug-eluting stents in a US Medicare setting: a cost-utility analysis with 3-year clinical follow-up data." Value in health 12, No. 5 (2009): 349-656.
Wang, Xiaoyin, et al. "Cost comparison of four revascularisation procedures for the treatment of multivessel coronary artery disease." Journal of medical economics 11.1 (2008).
Amin, Amit P., et al. "Use of drug-eluting stents as a function of predicted benefit: clinical and economic implications of current practice " Archives of internal medicine 172.15 (2012): 1145-1152.

\* cited by examiner

Fig. 1

METHOD TO IDENTIFY OPTIMUM CORONARY ARTERY DISEASE TREATMENT

Efficacious treatment and management of patients with Coronary Artery Disease (CAD) has drawn a great deal of attention especially because of the high prevalence and high mortality rate of coronary artery disease. Two major treatment options are Coronary Artery Bypass Grafting (CABG) and Percutaneous Coronary Intervention (PCI). CABG is more invasive and more expensive, however, the overall prognosis for CABG patients is better than the prognosis for PCI patients. PCI is a less expensive and a minimally-invasive option. The PCI procedure can be with untreated (bare metal) stents or with drug eluting stmts.

About one third of all patients who undergo the PCI procedure using bare metal stents (BMS) require a repeat procedure after several years. This is primarily due to restenosis at the site of the stent, requiring subsequent Target Vessel Revascularization (TVR). With the advent of Drug Eluting Stents (DES), the restenosis rate has been significantly reduced. However, these coated stents increase the low rate of life-threatening in-stent thrombosis events that are categorized as Major Adverse Cardiac Events (MACE).

SUMMARY

An embodiment of the present invention provides a method of identifying an optimum treatment a patient suffering from coronary artery disease, the method includes:
(i) providing one or more items of patient information selected from: (A) status in the patient of one or more biomarkers associated with coronary heart disease; (B) one or more items of medical history information of the patient selected from prior condition history, medical intervention history and medication history; (C) one or more items of diagnostic history of the patient, if the patient has a diagnostic history; and (D) one or more items of patient demographic data;
(ii) aggregating the patient information in one of: (a) a Bayesian network; (b) a machine learning and neural network; (c) a rule-based system; and (d) a regression-based system;
(iii) deriving a predicted probabilistic adverse event outcome for each intervention comprising percutaneous coronary intervention by placement of a bare metal stent, or a drug-coated stent; or by coronary artery bypass grafting; and
(iv) determining the intervention having the lowest predicted probabilistic adverse outcome.

Another embodiment of the present invention further provides a method of categorizing coronary artery disease in a patient, the method includes:
(i) providing one or more items of patient information selected from: (A) status in the patient of one or more biomarkers associated with coronary heart disease; (B) one or more items of medical history information of the patient selected from prior condition history, medical intervention history and medication history; (C) one or more items of diagnostic history of the patient, if the patient has a diagnostic history; and (D) one or more items of patient demographic data;
(ii) aggregating the patient information in one of: (a) a Bayesian network; (b) a machine learning and neural network; (c) a rule-based system; and (d) a regression-based system;
(iii) deriving a predicted probabilistic adverse event outcome for each coronary intervention selected from a percutaneous coronary intervention by placement of a bare metal stent, or a drug-coated stent; or by a coronary artery bypass graft; and
(iv) categorizing the coronary heart disease of the patient as most susceptible to treatment with percutaneous coronary intervention by placement of a bare metal stent, or a drug-coated stent; or by coronary artery bypass grafting, according to the lowest probabilistic adverse outcome prediction outcome for each of coronary intervention.

Another embodiment of the present invention further provides a method of treating a patient suffering from coronary artery disease, the patient having a plurality of biomarkers associated with coronary heart disease, a medical history, a diagnostic history and patient demographic data; the method includes:
(i) providing one or more items of patient information selected from: (A) status in the patient of one or more biomarkers associated with coronary heart disease; (B) one or more items of medical history information of the patient selected from prior condition history, medical intervention history and medication history; (C) one or more items of diagnostic history of the patient, if the patient has a diagnostic history; and (D) one or more items of patient demographic data;
(ii) aggregating the patient information in one of: (a) a Bayesian network; (b) a machine learning and neural network; (c) a rule-based system; and (d) a regression-based system;
(iii) deriving a predicted probabilistic adverse event outcome for each of percutaneous coronary intervention by placement of a bare metal stent, or a drug-coated stent; or by coronary artery bypass grafting; and
(iv) initiating treatment of the patient with percutaneous coronary intervention by placement of a bare metal stent, or a drug-coated stent; or by coronary artery bypass grafting, whichever has the lowest predicted probabilistic adverse outcome.

DETAILED DESCRIPTION

Coronary artery disease is associated with reduced blood flow through one or more of the coronary arteries. Restriction of blood flow in one or more of the coronary arteries can produce chest discomfort, known as angina. If severe, the artery can suddenly become completely occluded, disrupting the oxygen transport to the heart muscle, which causes Myocardial Infarction (MI) commonly referred to as a heart attack. The treatment to relieve the blockage through an invasive procedure is called revascularization. The presence or absence of the blockage is usually determined by cardiac catheterization procedures, which involves use of x-ray and a radio-opaque contrast agent.

Coronary Artery Bypass Grafting (CABG) is a surgical revascularization procedure, whereby a graft is used to repair the blocked coronary artery. A less invasive option is PCI, which involves transluminal placement of a metallic prosthesis called a stent (either a bare metal type: BMS, or a drug eluting type: DES). Prognosis following these procedures depends on a variety of factors and it is not well-understood [Stankovic Goran et al., Prediction of Restenosis After Coronary Angioplasty by Use of a New Index: TIMI Frame Count/Minimal Luminal Diameter Ratio, Circulation 2000; 101; 962-968]. There are recent studies on CABG versus PCI on large cohorts of patients that demonstrate long-term outcomes favoring CABG, when it comes to the number of repeat procedures required [Sec Denny D. F., Prediction of Restenosis after carotid artery Stent Implantation, Radiology 2003; 227; and 316-318. Hannan E L et al., Long-term outcomes of coronary-artery bypass grafting versus stent implantation, N Engl J Med. 2005 May 26; 352(21):2174-83].

It is beneficial to both patients and payers to have the appropriate therapy option with the highest efficacy (the optimum coronary artery treatment) for each patient group. According to an embodiment of the present invention, patients groups are based on specific characteristics expressed in in-vitro diagnostic measurements, imaging based information, and other diagnostic and demographics data. The high efficacy achieved in this embodiment is primarily due to the lower rate of subsequent Target Vessel Revascularization (TVR) and Major Adverse Cardiac Events (MACE) after the therapeutic procedure. Additionally, the identification of this patient group within the early months after Percutaneous Coronary Intervention (PCI) could also lead to better management through targeted administration of (possibly invasive) tests such as for instance optical coherence tomography (OCT) to characterize and quantify the disease process and the associated risk of adverse events. In one embodiment, the invention provides a set blood borne biomarkers and diagnostic information and an algorithm to aggregate the information, providing the probability of a specific patient belonging to the groups with high or low risk of Major Adverse Cardiac Events (MACE) after the therapeutic procedure, or high or low risk of Target Vessel Revascularization (TVR) after Percutaneous Coronary Intervention (PCI) using a bare metal stent or a drug eluting stent.

Neointimal hyperplasia is regarded as the main cause of in-stent restenosis (ISR). This proliferative process can be considered as healing of the arterial wall in response to the acute mechanical injury provoked by stent deployment (including for instance, injury of the endothelial cell lining, denudation and/or disruption of the lamina elastica, etc). The acute early phase of TSR is characterized by the activation of platelets and ensuing thrombosis accompanied by the recruitment into the intimal area of blood-borne monocytes, neutrophils and lymphocytes. These cells engage in the production of a plethora of mitogenic and chemotactic factors which trigger a chronic inflammatory response leading to the activation of the smooth muscle cells (SMCs) residing in the tunica media, which then undergo aberrant cell proliferation and migration toward the growing neointimal lesion. At later stages, post-PCI is characterized by the resolution of inflammation and wound healing, neointimal SMCs return to a contractile phenotype characterized by low proliferative and migratory activity and production of extracellular matrix (ECM) components to more closely resemble the undamaged arterial wall.

The therapeutic principle is derived from the pathophysiological evidence that ISR can be viewed as a proliferative disorder, mainly involving proliferation and migration of SMCs to form the patho-anatomical correlate of restenosis, the neointimal lesion. Lipophilic drugs that target the eukaryotic cell cycle, such as the G1-phase inhibitors sirolimus (also named rapamycin), Everolimus and Biolimus, or the S-phase inhibitor paclitaxel (also named taxol), are locally delivered at high local dosages via the stent surface into the adjacent vascular wall, thus attenuating cell proliferation and consequently in-stent restenosis (ISR). To modulate release kinetics of the drug, the vast majority of clinically available drug-eluting stents (DESs) utilize a polymeric coating. Due to non-specific anti-proliferative drug effects that also prevent endothelial proliferation, the healing process can be prolonged subsequent to placement of a DES compared to a bare metal stent (BMS). To prevent life-threatening stent thrombosis, the healing phase must be bridged by a longer-lasting dual anti-platelet therapy. The majority of therapeutic developments are based on the principle of local stent or device-based therapy and focus on coatings with less interference or improvements of the healing process, while maintaining anti-restenotic efficacy. Alternatively, they concentrate on biodegradable stent platforms as drug carriers that dissolve over time. Additional optimization of these factors could also comprise the development of tailored DESs adjusted to the unique needs of special lesion or patient subsets such as diabetics or patients suffering from an acute myocardial infarction [See for instance: Schomig A, et al., Prevention of restenosis by systemic drug therapy: back to the future? Circulation (2005) 112:2759-2761].

Known predictors of in-stent restenosis (ISR), which are directly related to prognosis, are limited to certain clinical scenarios, such as diabetes mellitus or previous ISR, as well as the number of stents per lesion, stent length, lesion length and complexity, residual diameter stenosis, and small vessel diameter (<2.75 mm) Many of these predictors can be quantified using invasive and non-invasive imaging tests [Mehran R et al., Angiographic Patterns of In-Stent Restenosis Classification and Implications for Long-Term Outcome, Circulation. 1999; 100:1872-1878; and Denny D. F., supra.].

Assuming that the risk of developing restenosis may have a genetic component, pilot genotype-phenotype studies have been conducted in small cohorts which identified the association between the risk of restenosis and single nucleotide polymorphisms (SNPs)/haplotypes in several genes considered involved in the disease. Validation of these preliminary results in larger cohorts, together with high-throughput screening for additional SNPs—the human genome contains millions of SNPs—may help identify useful markers for improved stratification of patients to individually tailored treatment for ISR [van Tiel, C. et al., p27kip1-838C>A Single Nucleotide Polymorphism Is Associated With Restenosis Risk After Coronary Stenting and Modulates p27kip1 Promoter Activity, Circulation (2009) 120 (8): 669].

Restenotic lesions typically lack lipid deposits and grow during 4-6 months post-stent implantation in Percutaneous Coronary Intervention (PCI), unlike native atheromas, which normally accumulate high content of lipids and develop over longer time periods, typically years or decades. Despite this, since the environment for the progression is the same, we hypothesize that there might be a weak correlation between various serum biomarkers (e.g., inflammation measure by C-reactive protein) and morphological biomarkers from imaging tests on one hand and in-stent restenosis and thrombosis events on the other hand [Jensen M. B., et al., The Promise and Potential Pitfalls of Serum Biomarkers for Ischemic Stroke and Transient Ischemic Attack, Neurologist. 2008 July; 14(4): 243-246; and Chan D. et al., Biomarkers in Acute Myocardial Infarction, Medicine 2010, 8:34].

In one embodiment the present invention provides methods to identify the best, most relevant combination of biomarkers to provide a risk score for Target Vessel Revascularization (TVR) and Major Adverse Cardiac Events (MACE) after a cardiac therapeutic procedure. Table 1 provides a non-limiting list of candidate cardiac biomarkers which may be screened and used in conjunction with imaging results and other diagnostic information in an embodiment of the present invention.

In one embodiment the present invention provides a method of identifying an optimum treatment a patient suffering from coronary artery disease, the method includes:
(i) providing one or more items of patient information selected from: (A) status in the patient of one or more biomarkers associated with coronary heart disease; (B) one or more items of medical history information of the patient selected from prior condition history, medical intervention history and medication history; (C) one or more items of diagnostic history of the patient, if the patient has a diagnostic history; and (D) one or more items of patient demographic data;
(ii) aggregating the patient information in one of: (a) a Bayesian network; (b) a machine learning and neural network; (c) a rule-based system; and (d) a regression-based system;
(iii) deriving a predicted probabilistic adverse event outcome for each intervention comprising percutaneous coronary intervention by placement of a bare metal stent, or a drug-coated stent; or by coronary artery bypass grafting; and
(iv) determining the intervention having the lowest predicted probabilistic adverse outcome, wherein the intervention having the lowest predicted probabilistic adverse outcome is selected from: percutaneous coronary intervention by placement of a bare metal stent, or a drug-coated stent; percutaneous coronary intervention by placement of a drug-coated stent and coronary artery bypass grafting.

TABLE 1

Biomarkers associated with Coronary Artery Disease

| PATHWAY | MARKER | ELISA KIT AVAILABLE |
| --- | --- | --- |
| Extracellular Matrix Markers | PIIINP | Yes |
|  | Tenascin-X | Yes |
| Matrix Degrading Enzymes | TIMP-1 | Yes |
|  | MMP-3 | Yes |
|  | MMP-9 | Yes |
| Thrombus Associated Proteins | Fibrinogen | Yes |
|  | D-dimer | Yes |
|  | Activated Protein C: C-inhibitor complex |  |
|  | tPA | Yes |
| Inflammation | IL-6 | Yes |
|  | IL-1 | Yes |
|  | IL-2 | Yes |
|  | TNF | Yes |
|  | CRP | Yes |
|  | Osteopontin | Yes |
|  | Resistin | Yes |

TABLE 1-continued

Biomarkers associated with Coronary Artery Disease

| PATHWAY | MARKER | ELISA KIT AVAILABLE |
| --- | --- | --- |
|  | Leptin | Yes |
|  | Adiponectin | Yes |
|  | sCD28 | Yes |
|  | sCD86 | Yes |
|  | sCTLA-4 | Yes |
|  | sVCAM-1 | Yes |
|  | sICAM-1 | Yes |
|  | Endothelin 1/2 | Yes |
| Lipids | HDL | Yes |
|  | LDL | Yes |
|  | Lipoprotein-A | Yes |
|  | Apoliporotein-A/B | Yes |

In another embodiment the method provides a determination that the lowest predicted probabilistic adverse outcome includes a low probability of a major adverse cardiac event (MACE). In another embodiment, the method provides a determination that the lowest predicted probabilistic adverse outcome includes a low probability of a target vessel revascularization (TVR). In another embodiment, the method provides a determination that the lowest predicted probabilistic adverse outcome includes a low probability of both a target vessel revascularization (TVR) and of a major adverse cardiac event (MACE).

In another embodiment the present invention provides a method of identifying an optimum treatment a patient suffering from coronary artery disease, wherein the status in the patient of one or more biomarkers associated with coronary heart disease includes the status of one or more of: PIIINP, Tenascin-X, TIMP-1, MMP-3, MMP-9, fibrinogen, D-dimer, Activated protein C: C-inhibitor complex, tPA, IL-6, IL-1, IL-2, TNF, CRP, osteopontin, resistin, leptin, adiponectin, sCD28, sCD86, sCTLA-4, sVCAM-1, sICAM-1, endothelin-1, endthelin-2, HDL, LDL, lipoprotein-A and apolipoprotein A/B.

In still another embodiment the present invention provides a method of identifying an optimum treatment a patient suffering from coronary artery disease, wherein the medical history of the patient includes one or more data points selected from CREA, CK, CKMB, Troponin, CRP, LDL, HDL and Fibrinogen.

In another embodiment the present invention provides a method of categorizing coronary artery disease in a patient, the method includes:
(i) providing one or more items of patient information selected from: (A) status in the patient of one or more biomarkers associated with coronary heart disease; (B) one or more items of medical history information of the patient selected from prior condition history, medical intervention history and medication history; (C) one or more items of diagnostic history of the patient, if the patient has a diagnostic history; and (D) one or more items of patient demographic data;
(ii) aggregating the patient information in: (a) a Bayesian network; (b) a machine learning and neural network; (c) a rule-based system; and (d) a regression-based system;
(iii) deriving a predicted probabilistic adverse event outcome for each coronary intervention selected from a percutaneous coronary intervention by placement of a bare metal stent, or a drug-coated stent; or by a coronary artery bypass graft; and (iv) categorizing the coronary heart disease of the patient as most susceptible to treatment with percutaneous coronary intervention by placement of a bare metal stent.

In another embodiment the present invention provides a method of treating a patient suffering from coronary artery disease, the patient having a plurality of biomarkers associated with coronary heart disease, a medical history, a diagnostic history and patient demographic data; the method includes:

(i) providing one or more items of patient information selected from: (A) status in the patient of one or more biomarkers associated with coronary heart disease; (B) one or more items of medical history information of the patient selected from prior condition history, medical intervention history and medication history; (C) one or more items of diagnostic history of the patient, if the patient has a diagnostic history; and (D) one or more items of patient demographic data;

(ii) aggregating the patient information in: (a) a Bayesian network; (b) a machine learning and neural network; (c) a rule-based system; and (d) a regression-based system;

(iii) deriving a predicted probabilistic adverse event outcome for each of percutaneous coronary intervention by placement of a bare metal stent, or a drug-coated stent; or by coronary artery bypass grafting; and (iv) initiating treatment of the patient with percutaneous coronary intervention by placement of a bare metal stent, or a drug-coated stent; or by coronary artery bypass grafting, whichever has the lowest predicted probabilistic adverse outcome.

In one embodiment the method provides a determination that the treatment with the lowest predicted probabilistic adverse outcome includes a low probability of a major adverse cardiac event (MACE). In another embodiment, the method provides a determination that that the treatment with the lowest predicted probabilistic adverse outcome includes a low probability of a target vessel revascularization (TVR). In another embodiment, the method provides a determination that the treatment with lowest predicted probabilistic adverse outcome includes a low probability of both a target vessel revascularization (TVR) and of a major adverse cardiac event (MACE).

In one embodiment, the method of the invention involves integrating information from a number of biomarkers with prognostic value post-percutaneous coronary intervention revascularization and major adverse cardiac events in order provide a personalized therapy to reduce the mortality rate due to a cardiac event, the rate of non-fatal MI events, and the number of repeat revascularization procedures. The focus is on identifying existing scrum blood-borne biomarkers, which individually have weak predictive value in assessing the risk and the outcome of the percutaneous coronary intervention (PCI) for both the bare metal stent and the drug-eluting stent treatments. A computerized decision support is then used to integrate the output of the following tests: a) In-vitro biomarkers, including serum tests, such as for instance and without limitation, those listed in Table 1, covering a number of different pathways. In additional, in the extension of this embodiment, results of molecular/genetic tests including assessment of single nucleotide polymorphisms (SNPs) or genome sequencing, etc.; b) medical history information, such information as the patient's prior conditions, interventions, or medications; c) diagnostic information, capturing clinical expert opinion regarding the current state of the disease and the patient overall health assessment. Specifically, this includes the geometric information regarding the characteristic of the occlusion; and d) demographic information, which may include, but is not limited to patient gender, age, race, smoking or not smoking etc.

All these items of information are aggregated to an algorithm that segregates risk factor for both TVR and MACE under BMS, DES and CABG treatment options, respectively. The methodologies for integrating this information can be but not limited to: a) Bayesian Network, which is a knowledge-based graphical representation showing variables and probabilistic relationships among them. Based on a series of data with known outcome, the network can be established, and based on that the system can assess the probability of an outcome once new data is available; b) Machine learning and Neural Network, in which the system is able to model the relationship among sets of data, without specific input from an expert regarding the relationship among the data. The interpretation of the outcome based on a new set of data may be seen as a machine learnt interpolation (regression) procedure; c) Rule Based System, where the knowledge of domain experts are captured and expressed using a set of rules which are chained based on the sequence of events to predict an outcome. In addition to directed approaches where clinical data along with the outcome is required, it would be possible to use undirected clustering schemes to identify groups of populations which demonstrate similar pattern with the available clinical data, and predict the outcome with the data which is not fully characterized. Finally, d) Regression based System, which is completely based on undirected set of input data and specific outcome for both TVR and MACE under two treatment options of BMS and DES, respectively.

Figure 1:
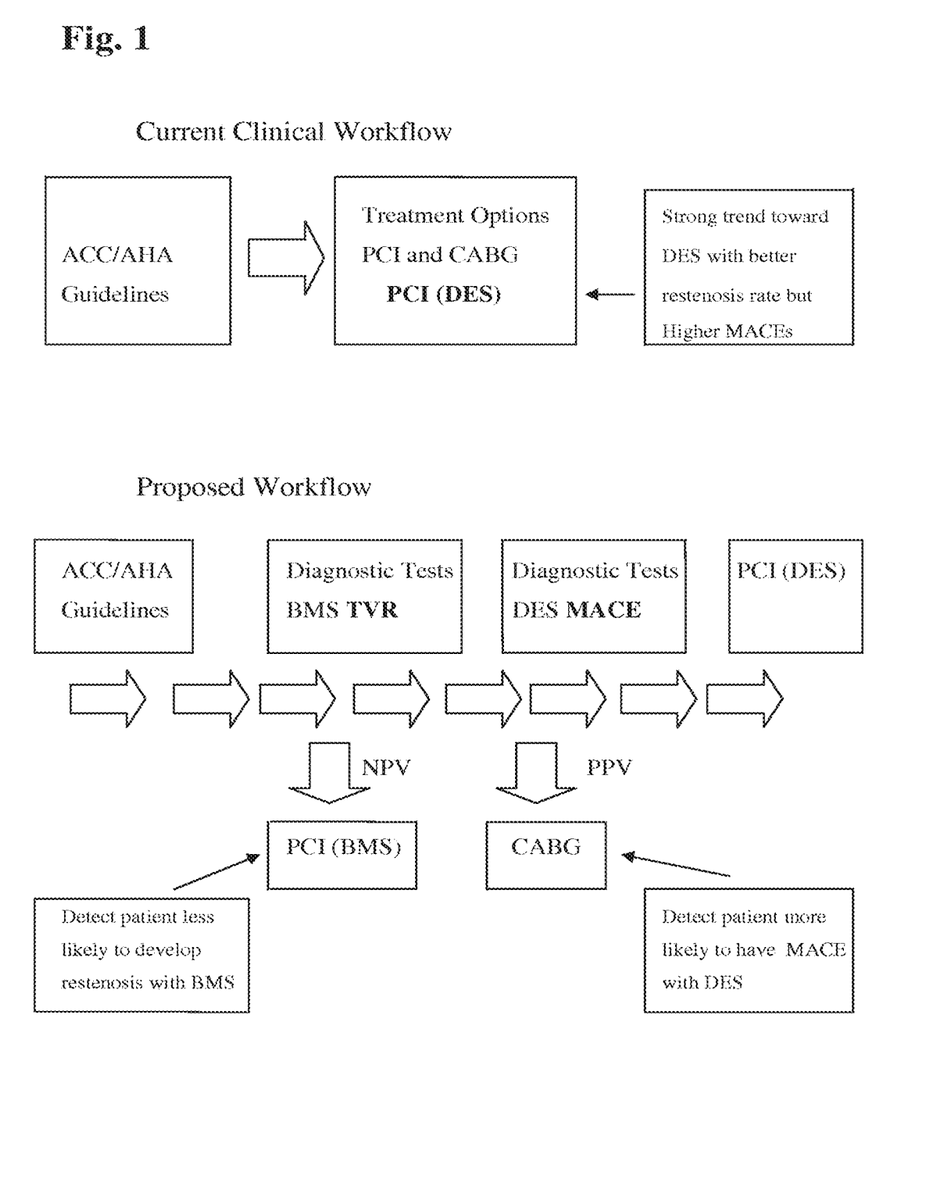
FIG. 1 shows an example of a current clinical workflow and an embodiment of the combined tests of the invention, illustrating the way the two-parameter tests of TVR and MACE are cascaded to derive a recommendation for the treatment and management of patients with coronary artery disease.

As shown in FIG. 1 the usual current clinical workflow shows a strong trend towards PCI using drug-eluting stents, resulting in a lower incidence of restenosis but resulting in an elevated rate of major adverse cardiac events (MACE); also shown is an embodiment of the combined tests of the invention, illustrating the way the target vessel revascularization (TVR) and (MACE) are cascaded in a two-test to derive a recommendation for the treatment and management of patients with coronary artery disease.

A first test is performed to answer whether the patient is a candidate for treatment with a bare metal stent (BMS). In cases where the patient has a low risk of developing restenosis (hence requiring a revascularization) within 6 months of initial treatment, the conclusion is that the patient would benefit from BMS and can be routed to this treatment option to avoid possible major adverse cardiac events (MACE) which are associated with drug-eluting stents (DES). In order to make this determination with confidence, the Negative Predictive Value of such test must be high. In other words, the percentage of patients who are wrongly routed to this option must be as small as possible. For the patients with positive restenosis/target vessel revascularization (TVR) results, a second test is performed: The focus of the second test is to identify the risk of having a MACE event should the DES treatment be selected. If the risk is high, the better alternative choice will be cardiac artery bypass grafting (CABG), which is known to have a MACE rate significantly lower than DES despite its higher cost and invasive nature. By contrast, if the risk of MACE is low, the best option is limited to treatment with a drug-eluting stent (DES). Compared to the present state of the practice, with its tendency to use DES as the major treatment option, the stratified approach as proposed herein produces both cost benefits and overall increased efficacy as compared to the use of treatment with a DES alone.

The inventors have performed a series of tests according to an embodiment of the present invention, based on data from various patient groups separated by age, sex, diabetic condition which included a number of biomarkers, specifically, CREA, CK, CKMB, troponin, CRP, LDL, HDL, fibrinogen and also diagnostic information such as history of myocardial infarction, family history of cardiac disease, stenosis type, stenosis length and diameter, body mass index (BMI), hypertension, diabetes condition, American Heart Association (AHA) category, ST segment elevation characteristic, etc. The goal was to find a combination of these attributes which predict TVR and MACE under BMS and DES treatment options, respectively.

The combination of these attributes was optimized to provide maximum negative predictive value (NPV) for TVR under BMS and maximum positive predictive value for MACE under DES treatment option. The results are shown in the Tables 2 and 3 below.

Table 2 at cut 2 (underlined and marked with an asterisk) demonstrates that the algorithmic test provides an NPV of 0.928 (p-value=0.012 CI 95%=[0.85, 0.98]), which is significantly higher than 0.811 noted as the prior distribution of patients without stenosis under BMS. Moreover the specificity of the test is 45%, which indicates that about 45% of patient who would not draw benefit from BMS can be detected using this test. However, the NPV of 0.928 indicates that only fewer than 8% patients with negative outcome would be wrongly classified as "not having a high risk of restenosis."

Table 3 shows the same principle applied for detecting patients with high risk of MACE under a DES treatment condition. At cut 1, (underlined and marked with an asterisk) the Positive Predictive Value of this test is 0.765 which is a significant improvement over the baseline positive percentage of 0.273. The sensitivity of 43% indicates that significant portion of patients can be detected correctly using this test.

TABLE 2

Results for Patient Groups for Restenosis Detection Based on BMS Treatment.

| CUT | Positive | Negative | NPV | PPV | Baseline (NPV; PPV) | AUC | Accuracy | Specificity | Sensitivity |
|---|---|---|---|---|---|---|---|---|---|
| 1 | 20 | 86 | 0.956 | 0.228 | (0.811, 0.819) | 0.639 | 0.382 | 0.250 | 0.950 |
| 2* | 20 | 86 | 0.928 | 0.264 | (0.811, 0.819) | 0.675 | 0.525 | 0.450 | 0.850 |
| 3 | 24 | 88 | 0.901 | 0.265 | (0.786 0.214) | 0.610 | 0.459 | 0.350 | 0.859 |
| 4 | 54 | 165 | 0.811 | 0.353 | (0.753 0.247) | 0.626 | 0.651 | 0.700 | 0.501 |
| 5 | 52 | 137 | 0.790 | 0.355 | (0.725 0.275) | 0.582 | 0.594 | 0.600 | 0.579 |

Definition of the Groups Defining the "Cut"

| CUT | AGE | SEX | DIABETES | BIOMARKER | DIAGNOSTIC |
|---|---|---|---|---|---|
| 1 | >60 (2) | Female (1) | All (0) | None (0) | Yes (2) |
| 2 | >60 (2) | Female (1) | All (0) | (2) CREA, CK, CKMB, Troponin, CRP | Yes (2) |
| 3 | >60 (2) | Female (1) | No Diabetes (1) | (1) | No (0) |
| 4 | >60 (2) | All (0) | No Diabetes (1) | None (0) | Yes (1) |
| 5 | >60 (2) | Male (2) | No Diabetes (1) | None (0) | Yes (2) |

TABLE 3

Results for Patient Groups for MACE Detection Based on DES Treatment.

| CUT | Positive | Negative | NPV | PPV | Baseline (NPV; PPV) | AUC | Accuracy | Specificity | Sensitivity |
|---|---|---|---|---|---|---|---|---|---|
| 1* | 30 | 80 | 0.817 | 0.765 | (0.727, 0.273) | 0.714 | 0.810 | 0.95 | 0.433 |
| 2 | 160 | 494 | 0.812 | 0.675 | (0.755, 0.245) | 0.694 | 0.796 | 0.95 | 0.321 |
| 3 | 147 | 541 | 0.826 | 0.591 | (0.786 0.214) | 0.653 | 0.804 | 0.95 | 0.265 |
| 4 | 152 | 543 | 0.850 | 0.371 | (0.781 0.219) | 0.653 | 0.701 | 0.75 | 0.527 |
| 5 | 186 | 745 | 0.847 | 0.344 | (0.8 0.2) | 0.631 | 0.724 | 0.8 | 0.419 |

Definition of the Groups Defining the "Cut"

| CUT | AGE | SEX | DIABETES | BIOMARKER | DIAGNOSTIC |
|---|---|---|---|---|---|
| 1 | <60 (1) | All (0) | With Diabetes (2) | (3) CRP, CREA, DbTNT, parallel TNT, HsTNT, NTproBNP | No (0) |
| 2 | >60 (2) | All (0) | No Diabetes (1) | Same as cut 1 (3) | Yes (1) |
| 3 | All (0) | Male (2) | No Diabetes (1) | Same as cut 1 (3) | Yes (1) |
| 4 | >60 (2) | Male (2) | No Diabetes (1) | Same as cut 1 (3) | No (0) |
| 5 | All (0) | Male (2) | No Diabetes (1) | Same as cut 1 (3) | No (0) |

Figure 2:
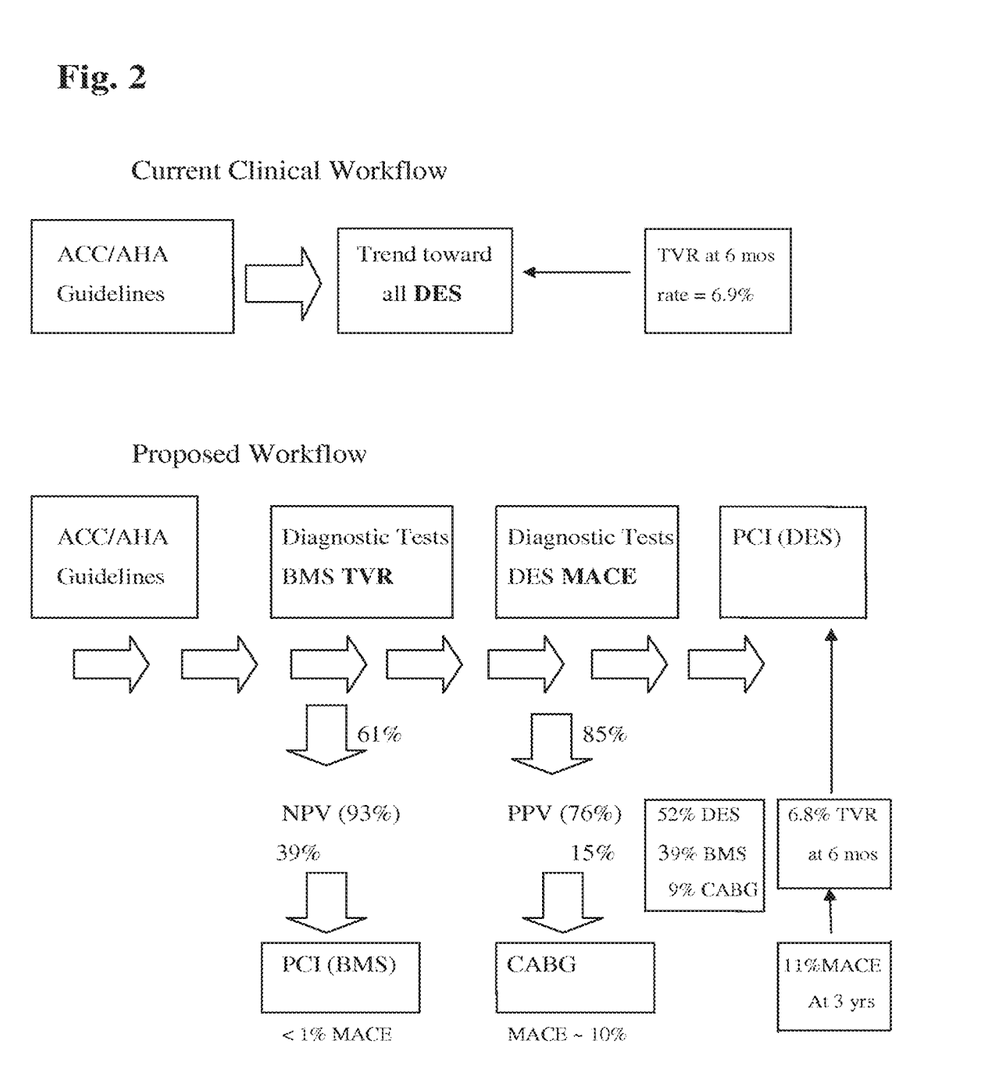
FIG. 2 shows a representation of the current clinical workflow according to the American College of Cardiologists/American Heart Association (ACC/AHA) guidelines; and an example of a cascaded tests of the invention providing a recommended stratification of treatments for patients: 52% recommended for drug-eluting stents, 29% recommended for bare metal stents, and 9% recommended for coronary artery bypass grafting as compared to current clinical practice of prescribing drug-eluting stents for all patients.

As shown in the FIG. 2, the cascaded tests of the present invention as compared to current clinical practice of prescribing DES for all patients, provides a stratification consisting of 52% DES, 29% BMS, and 9% CABG. Overall the combined test provides a TVR rate of 6.8%, which is comparable with DES only option, whereas the MACE rate improves from 27% to only 11%. A cost-benefit analysis demonstrates that 85.7% of the total patient population would benefit from the proposed test, while only 4.9% of overall patients would not be correctly diagnosed. These results compare to an overall 27.3% of wrongly diagnosed patients in the currently accepted workflow of patient allocation according to ACC/AHA guidelines. While the overall cost of the procedure is virtually unchanged, the economic impact of the inaccurate diagnosis for the currently recommended workflow using DES treatment only is about $14,000 per patient treated. This amount is reduced to about $6,500 for the proposed test according to the methods of the present invention. Based on the assumption of a 10% adoption rate and a total relevant population of 144,000 patients per year in the United States, the overall saving to the US healthcare systems is over a $1 billion per year.

Despite the fact that the current results are based on the data from a single institution, the statistical margins obtained are sufficiently large that even in the eventuality that a larger sample were to diminish the performance number, the overall inventive concept would still remain viable in terms of both efficacy rates and cost effectiveness. The illustrated trained algorithm model is based on specific labels (radiological restenosis confirmed by angiography at 6 months and MACE events within three years), however, additional diagnostic information acquired post procedure may also be used as labels and predictors may be learned from such input data. Further, the learning algorithm may be modified from the directed to a random cut to detect clusters within the input data prior to treatment and perform a dimensionality reduction before directed learning and predicting a specific clinical indicator.

The examples and embodiments of the present invention provided herein are for illustration only and are not to be taken as limitations of the inventive concept. The full texts of the references cited herein are incorporated by reference in their entireties.

ADDITIONAL REFERENCES 1. http://hcupnet.ahrq.gov/HCUPnet.jsp
2. Hermus L, Lefrandt J D, Tio R A, Breek J C, Zeebregts C J., Carotid plaque formation and serum biomarkers, Atherosclerosis. 2010 May 19.
3. Dangas G., et al., Restenosis: Repeat Narrowing of a Coronary Artery: Prevention and Treatment, Circulation 2002; 105; 2586-2587.
4. Hitly K. C., et al., Vulnerable Plaque Imaging—Current Techniques, J. of Cardiovasc. Trans. Res. (2009) 2:9-18
5. Costa M A, Simon D I, Molecular basis of restenosis and drug-eluting stents, Circulation 2005, 111:2257-2273.
6. Wessely R, Schömig A, Kastrati A, Sirolimus and Paclitaxel on polymer-based drug-eluting stents: similar but different, J Am Coll Cardiol (2006) 47: 708-714.
7. Trikalinos T A, Dahabreh I J, Wong J, Rao M. Future Research Needs for the Comparison of Percutaneous Coronary Interventions with Bypass Graft Surgery in Nonacute Coronary Artery Disease: Identification of Future Research Needs from Comparative Effectiveness. Rockville (Md.): Agency for Healthcare Research and Quality (US); 2010 September Report No.: 10-EHC068-EF.
8. AHRQ Comparative Effectiveness Reviews.
9. Yock C A, Boothroyd D B, Owens D K, et al. Cost-effectiveness of bypass surgery versus stenting in patients with multivessel coronary artery disease. Am J Med. 2003 Oct. 1; 115(5):382-389.
10. Bischof M, Briel M, Bucher H C, et al. Cost-Effectiveness of Drug-Eluting Stents in a US Medicare Setting: A Cost-Utility Analysis with 3-Year Clinical Follow-Up Data. Value Health. 2009 Mar. 11.
11. Wang, X et al. Cost comparison of four revascularisation procedures for the treatment of multivessel coronary artery disease. Journal of Medical Economics 2008; 11: 119-134.

We claim:

1. A method of identifying an optimum treatment for a patient suffering from coronary artery disease, the method comprising:
   (i) providing one or more items of patient information selected from:
      (A) status in the patient of one or more biomarkers associated with coronary heart disease;
      (B) one or more items of medical history information of the patient selected from prior condition history, medical intervention history, and medication history;
      (C) one or more items of diagnostic history of the patient; and
      (D) one or more items of patient demographic data;
   (ii) aggregating the patient information in a machine learning and neural network; and
   (iii) determining a recommended intervention for the patient using a cascaded series of tests based on the aggregated patient information by:
      deriving, using the machine learning and neural network based on a first set of patient information input to the machine learning and neural network, a predicted probability of target vessel revascularization (TVR) for a bare metal stent percutaneous coronary intervention;
      in response to a determination that the predicted probability of TVR for the bare metal stent percutaneous coronary intervention is less than a first threshold, determining the bare metal stent percutaneous coronary intervention to be the recommended intervention for the patient;
      in response to a determination that the predicted probability of TVR for the bare metal stent percutaneous coronary intervention is not less than the first threshold, deriving, using the machine learning and neural network based on a second set of patient information input to the machine learning and neural network, a predicted probability of a major adverse cardiac event (MACE) for a drug-eluting stent percutaneous coronary intervention, wherein the second set of patient information includes patient age, patient gender, diabetes condition of the patient, diagnostic history information of the patient, and CRP, CREA, DbTNT, parallel TNT, HsTNT and NTproBNP biomarkers;
      in response to a determination that the predicted probability of a MACE for the drug-eluting stent percutaneous coronary intervention is not greater than a second threshold, determining the drug-eluting stent percutaneous coronary intervention to be the recommended intervention for the patient; and in response to a determination that the predicted probability of a MACE for the drug-eluting stent percutaneous coronary intervention is greater than the second threshold, determining a coronary artery bypass grafting to be the recommended intervention for the patient, wherein the machine learning and neural network models relationships among the first set of patient information and the predicted probability of TVR and among the second set of patient information and the predicted probability of a MACE without input from an expert regarding the relationships.

2. The method of claim 1, wherein the first set of patient information includes a patient age, patient gender, a diabetes condition of the patient, diagnostic history information of the patient, and CREA, CK, CKMB, troponin, and CRP biomarkers.

3. A method of treating a patient suffering from coronary artery disease, the method comprising:
(i) providing one or more items of patient information selected from:
   (A) status in the patient of one or more biomarkers associated with coronary heart disease;
   (B) one or more items of medical history information of the patient selected from prior condition history, medical intervention history, and medication history;
   (C) one or more items of diagnostic history of the patient; and
   (D) one or more items of patient demographic data;
(ii) aggregating the patient information in a machine learning and neural network;
(iii) determining a recommended intervention for the patient using a cascaded series of tests based on the aggregated patient information by:
   deriving, using the machine learning and neural network based on a first set of patient information input to the machine learning and neural network, a predicted probability of target vessel revascularization (TVR) for a bare metal stent percutaneous coronary intervention, wherein the first set of patient information includes patient age, patient gender, diabetes condition of the patient, diagnostic history information of the patient, and CREA, CK, CKMB, troponin and CRP biomarkers;
   in response to a determination that the predicted probability of TVR for the bare metal stent percutaneous coronary intervention is less than a first threshold, determining the bare metal stent percutaneous coronary intervention to be the recommended intervention for the patient;
   in response to a determination that the predicted probability of TVR for the bare metal stent percutaneous coronary intervention is not less than the first threshold, deriving, using the machine learning and neural network based on a second set of patient information input to the machine learning and neural network, a predicted probability of a major adverse cardiac event (MACE) for a drug-eluting stent percutaneous coronary intervention;
   in response to a determination that the predicted probability of a MACE for the drug-eluting stent percutaneous coronary intervention is not greater than a second threshold, determining the drug-eluting stent percutaneous coronary intervention to be the recommended intervention for the patient; and
   in response to a determination that the predicted probability of a MACE for the drug-eluting stent percutaneous coronary intervention is greater than the second threshold, determining a coronary artery bypass grafting to be the recommended intervention for the patient; and
(iv) initiating treatment of the patient with the recommended intervention determined for the patient,
wherein the machine learning and neural network models relationships among the first set of patient information and the predicted probability of TVR and among the second set of patient information and the predicted probability of a MACE without input from an expert regarding the relationships.

4. The method of claim 3, wherein the biomarkers associated with coronary heart disease comprise one or more biomarkers selected from PIIINP, Tenascin-X, TIMP-1, MMP-3, MMP-9, fibrinogen, D-dimer, Activated protein C: C-inhibitor complex, tPA, IL-6, IL-1m IL-2, TNF, CRP, osteopontin, resistin, leptin, adiponectin, sCD28, sCD86, sCTLA-4, sVCAM-1, sICAM-1, endothelin-1, endothelin-2, HDL, LDL, lipoprotein-A, and apolipoprotein NB.

5. The method of claim 3, wherein the first set of patient information input to the machine learning and neural network is selected to provide a maximum negative predictive value for the probability of TVR for the bare metal stent percutaneous coronary intervention in a set of training data from previous patients.

6. The method of claim 3, wherein the second set of aggregated patient information input to the machine learning and neural network is optimized to provide a maximum positive predictive value for the probability of a MACE for the drug-eluting stent percutaneous coronary intervention in a set of training data from previous patients.

7. A method of identifying an optimum treatment for a patient suffering from coronary artery disease, the method comprising:
(i) providing one or more items of patient information selected from:
   (A) status in the patient of one or more biomarkers associated with coronary heart disease;
   (B) one or more items of medical history information of the patient selected from prior condition history, medical intervention history, and medication history;
   (C) one or more items of diagnostic history of the patient; and
   (D) one or more items of patient demographic data;
(ii) aggregating the patient information in a machine learning and neural network; and
(iii) determining a recommended intervention for the patient using a cascaded series of tests based on the aggregated patient information by:
   deriving, using the machine learning and neural network based on a first set of patient information input to the machine learning and neural network, a predicted probability of target vessel revascularization (TVR) for a bare metal stent percutaneous coronary intervention, wherein the first set of patient information includes patient age, patient gender, diabetes condition of the patient, diagnostic history information of the patient, and CREA, CK, CKMB, troponin and CRP biomarkers;
   in response to a determination that the predicted probability of TVR for the bare metal stent percutaneous coronary intervention is less than a first threshold, determining the bare metal stent percutaneous coronary intervention to be the recommended intervention for the patient;

in response to a determination that the predicted probability of TVR for the bare metal stent percutaneous coronary intervention is not less than the first threshold, deriving, using the machine learning and neural network based on a second set of patient information input to the machine learning and neural network, a predicted probability of a major adverse cardiac event (MACE) for a drug-eluting stent percutaneous coronary intervention;

in response to a determination that the predicted probability of a MACE for the drug-eluting stent percutaneous coronary intervention is not greater than a second threshold, determining the drug-eluting stent percutaneous coronary intervention to be the recommended intervention for the patient; and in response to a determination that the predicted probability of a MACE for the drug-eluting stent percutaneous coronary intervention is greater than the second threshold, determining a coronary artery bypass grafting to be the recommended intervention for the patient, wherein the machine learning and neural network models relationships among the first set of patient information and the predicted probability of TVR and among the second set of patient information and the predicted probability of a MACE without input from an expert regarding the relationships.

8. The method of claim 7, wherein the biomarkers associated with coronary heart disease comprise one or more biomarkers selected from PIIINP, Tenascin-X, TIMP-1, MMP-3, MMP-9, fibrinogen, D-dimer, Activated protein C: C-inhibitor complex, tPA, IL-6, IL-1m IL-2, TNF, CRP, osteopontin, resistin, leptin, adiponectin, sCD28, sCD86, sCTLA-4, sVCAM-1, sICAM-1, endothelin-1, endothelin-2, HDL, LDL, lipoprotein-A, and apolipoprotein A/B.

9. The method of claim 7, wherein the first set of patient information input to the machine learning and neural network is selected to provide a maximum negative predictive value for the predicted probability of TVR for the bare metal stent percutaneous coronary intervention in a set of training data from previous patients.

10. The method of claim 7, wherein the second set of patient information input to the machine learning and neural network is optimized to provide a maximum positive predictive value for the predicted probability of a MACE for the drug-eluting stent percutaneous coronary intervention in a set of training data from previous patients.

11. The method of claim 7, wherein the second set of patient information input to the machine learning and neural network includes a patient age, patient gender, a diabetes condition of the patient, diagnostic history information of the patient, and CRP, CREA, DbTNT, parallel TNT, HsTNT, and NTproBNP biomarkers.

12. The method of claim 7, wherein a first set of biomarkers associated with coronary heart disease in the first set of patient information input to the machine learning and neural network is different from a second set of biomarkers associated with coronary heart disease in the second set of patient information input to the machine learning and neural network.

13. The method of claim 7, further comprising:
deriving, using the machine learning and neural network, a predicted probability of a MACE for the bare metal stent percutaneous coronary intervention based on the aggregated patient information.

14. The method of claim 7, further comprising:
deriving, using the machine learning and neural network, a predicted probability of TVR for the drug-eluting stent percutaneous coronary intervention based on the aggregated patient information.

15. The method of claim 7, further comprising:
deriving, using the machine learning and neural network, a predicted probability of a MACE for the coronary artery bypass grafting based on the aggregated patient information.

\* \* \* \* \*